(12) United States Patent
Shin et al.

(10) Patent No.: US 9,078,620 B2
(45) Date of Patent: Jul. 14, 2015

(54) X-RAY APPARATUS AND METHOD OF OBTAINING X-RAY IMAGE

(71) Applicant: Samsung Electronics Co., Ltd., Suwon-si (KR)

(72) Inventors: Seung-woo Shin, Yongin-si (KR); Jeong-hwan Kim, Seoul (KR); Do-kwan Oh, Suwon-si (KR); Dong-jae Lee, Hwaseong-si (KR); Sang-chul Lee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 91 days.

(21) Appl. No.: 14/046,227

(22) Filed: Oct. 4, 2013

(65) Prior Publication Data

US 2014/0105357 A1    Apr. 17, 2014

(30) Foreign Application Priority Data

Oct. 11, 2012    (KR) .................. 10-2012-0113042

(51) Int. Cl.
*H05G 1/02*    (2006.01)
*A61B 6/00*    (2006.01)

(52) U.S. Cl.
CPC ............ *A61B 6/4452* (2013.01); *A61B 6/4435* (2013.01); *A61B 6/5241* (2013.01)

(58) Field of Classification Search
CPC .. A61B 6/4452; A61B 6/5241; A61B 6/4435; H05G 1/02
USPC .......................................... 378/62, 193–198
See application file for complete search history.

(56) References Cited

U.S. PATENT DOCUMENTS

| | | | |
|---|---|---|---|
| 4,696,025 A * | 9/1987 | Taylor | 378/146 |
| 5,191,600 A | 3/1993 | Vincent et al. | |
| 6,895,076 B2 | 5/2005 | Halsmer et al. | |
| 6,944,265 B2 | 9/2005 | Warp et al. | |
| 7,142,632 B2 | 11/2006 | Atzinger et al. | |
| 7,555,100 B2 | 6/2009 | Wang et al. | |
| 2009/0015669 A1 | 1/2009 | Klingenbeck-Regn | |

FOREIGN PATENT DOCUMENTS

| | | |
|---|---|---|
| JP | 11-290307 A | 10/1999 |
| JP | 2002-350370 A | 12/2002 |
| JP | 2010-127810 A | 6/2010 |
| JP | 2012-130436 A | 7/2012 |
| KR | 10-2009-0078650 A | 7/2009 |

OTHER PUBLICATIONS

Communication dated Mar. 20, 2014 issued by the Korean Intellectual Property Office in counterpart Korean Patent Application No. 10-2012-0113042.
International Search Report and Written Opinion dated Jan. 7, 2014 issued by the International Searching Authority in counterpart Application No. PCT/KR2013/009075 (PCT/ISA/210 & PCT/ISA/237).
Communication dated Nov. 5, 2013 issued by the Korean Intellectual Property Office in counterpart Korean Patent Application No. 10-2012-0113042.

* cited by examiner

*Primary Examiner* — Courtney Thomas
(74) *Attorney, Agent, or Firm* — Sughrue Mion, PLLC

(57) ABSTRACT

An X-ray apparatus includes: a source for emitting X-rays to an object; a detector for detecting the X-rays penetrating the object; an arm for connecting the source to the detector and moving the detector up and down according to a rotation of the source; and a controller for controlling an imaging of the object by driving the arm.

21 Claims, 12 Drawing Sheets

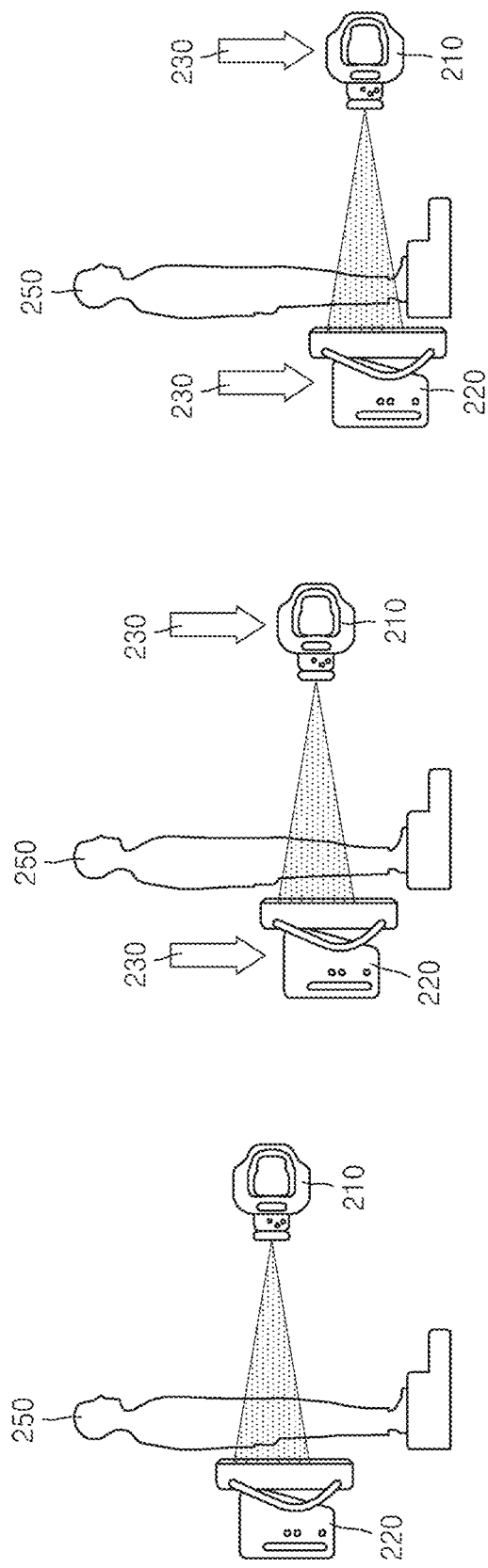

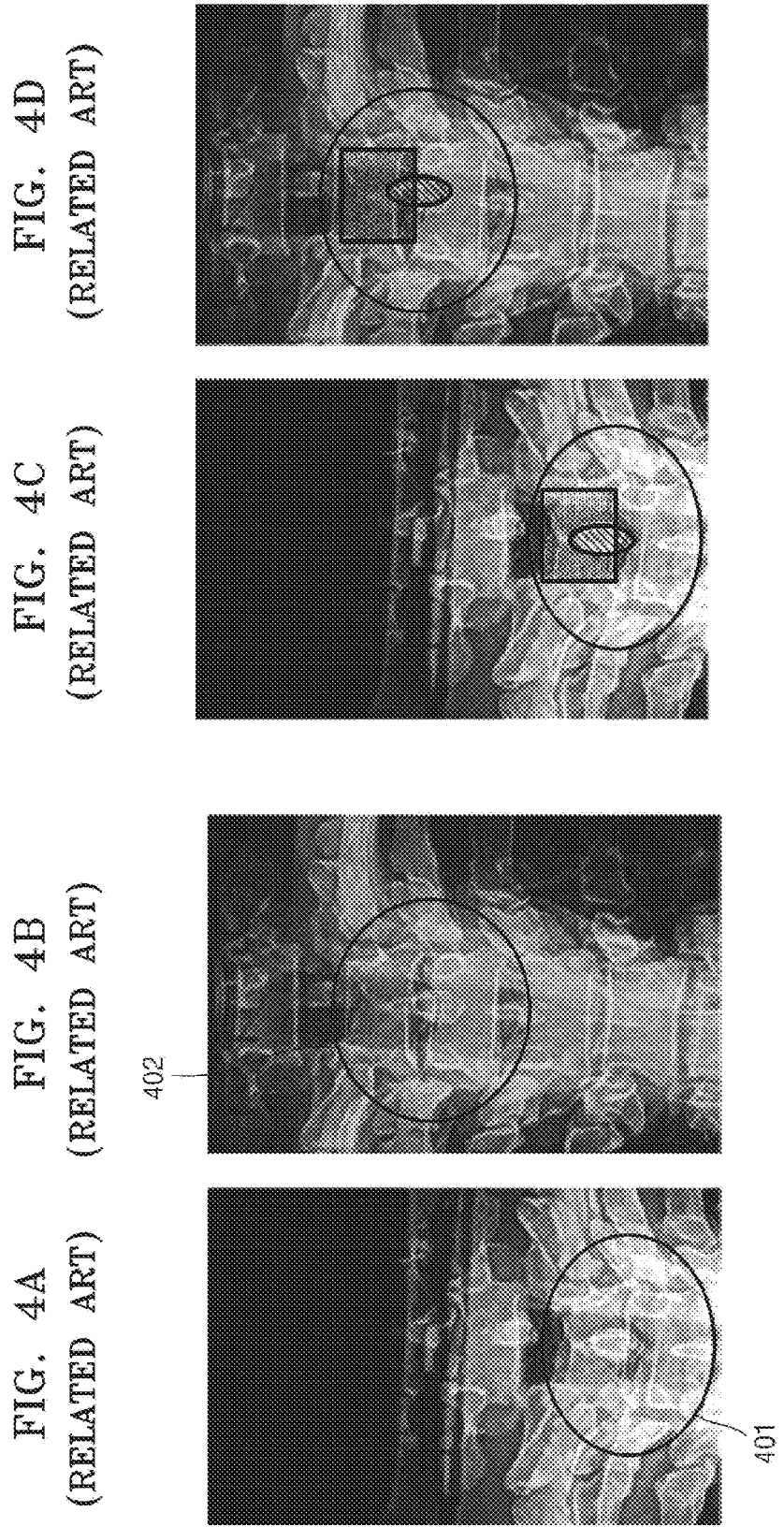

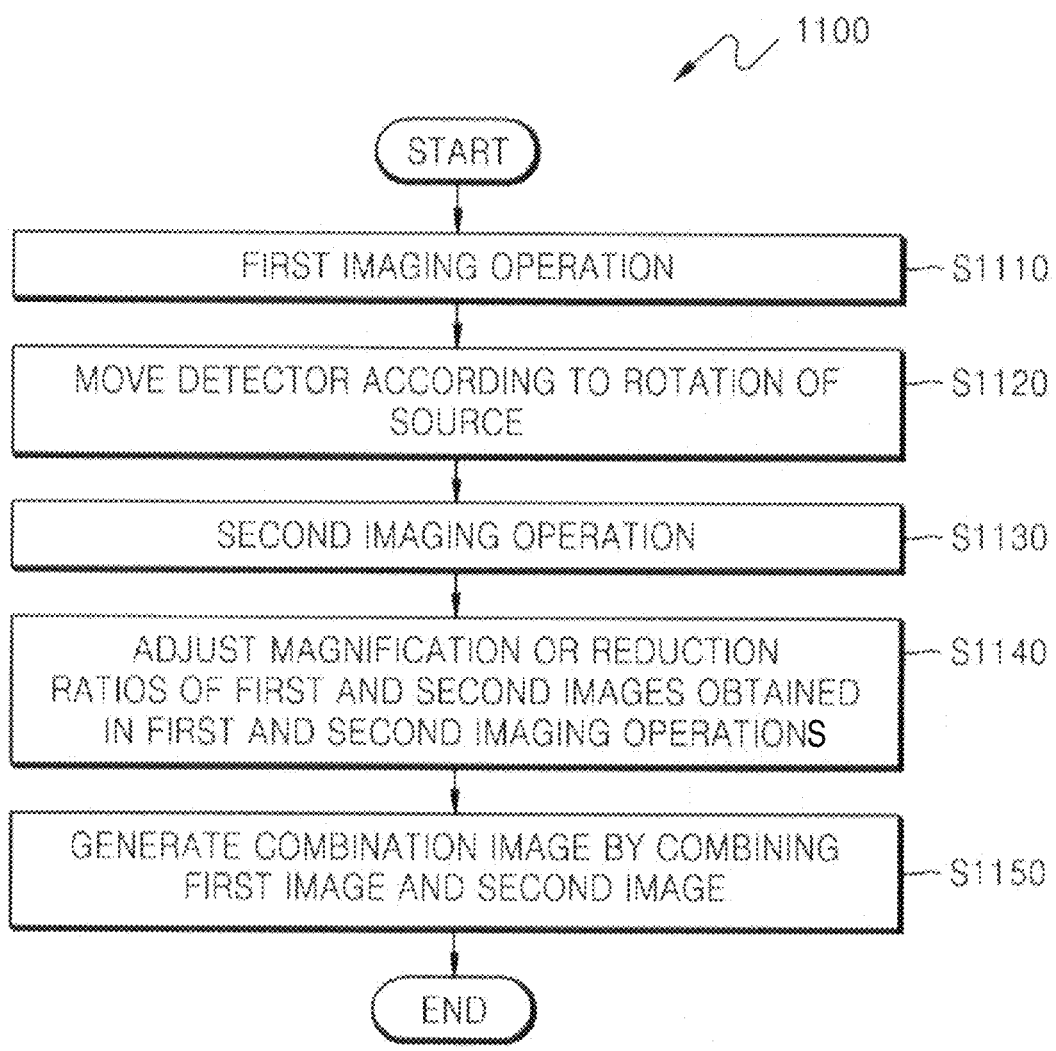

X-RAY APPARATUS AND METHOD OF OBTAINING X-RAY IMAGE

CROSS-REFERENCE TO RELATED PATENT APPLICATION

This application claims priority from Korean Patent Application No. 10-2012-0113042, filed on Oct. 11, 2012, in the Korean Intellectual Property Office, the disclosure of which is incorporated herein in its entirety by reference.

BACKGROUND

1. Field

Apparatuses and methods consistent with exemplary embodiments relate to capturing an X-ray image by using the X-ray apparatus, and more particularly, to obtaining X-ray images by driving the X-ray apparatus.

2. Description of the Related Art

When X-rays penetrate an object, the X-rays attenuate depending on the properties of the object and the distance to the object. An X-ray apparatus may image the internal areas or contents of the human body or objects by using such characteristics, and is widely used in medical imaging and industrial nondestructive testing.

An area of an object, which may be imaged at a time by the X-ray apparatus, may be limited to only a portion of the object based on the desired accuracy and/or resolution. Accordingly, an image stitching technique for obtaining an image having a larger area or higher resolution by combining a plurality of imaging images has been developed. The image stitching technique is generally performed by using computer software, and the irradiation of identical X-rays is needed to obtain an accurate overlap between separate images to be combined.

The X-ray apparatus includes an apparatus for generating X-rays and an apparatus for detecting the X-rays and converting the detected X-rays into an image. Examples of the X-ray apparatus include a ceiling-type X-ray apparatus and a U-arm-type X-ray apparatus.

In the ceiling-type X-ray apparatus, an apparatus for generating X-rays is fixed to a ceiling; thus, providing a wide operating range and easy access to imaging areas of a patient due to the flexibility of operation.

In the U-arm-type X-ray apparatus, an apparatus for generating X-rays and an apparatus for detecting the X-rays are fixed to an arm connected to an arm stand fixed on the ground. The U-arm-type X-ray apparatus has advantages in that an occupation space thereof is small and the price and installation costs thereof are lower, as compared to the ceiling-type X-ray apparatus. However, since an apparatus for generating X-rays and an apparatus for detecting the X-rays are fixed to an arm, the U-arm-type X-ray apparatus has disadvantages in that a degree of freedom is lower, thereby limiting a range of movement, as compared to the ceiling-type X-ray apparatus.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more of exemplary embodiments provide an X-ray apparatus for minimizing image distortion and obtaining an image for a large area.

According to an aspect of an exemplary embodiment, there is provided an X-ray apparatus including: a source for emitting X-rays to an object; a detector for detecting the X-rays penetrating the object; an arm for connecting the source to the detector and moving the detector up and down according to a rotation of the source; a support unit for supporting the arm; and a controller for controlling an imaging for the object by driving the arm.

The controller may control at least one of the source, the detector, and the arm, and may control a straight movement distance of an end of the arm connected to the detector based on an X-ray incident angle of X-rays that are emitted from the source to the detector.

The controller may control the straight movement distance of the end of the arm connected to the detector, in order to perform a second imaging, based on an X-ray incident angle in a first imaging.

The controller may control the arm so that the X-ray incident angle in the first imaging and an X-ray incident angle in the second imaging correspond to each other, in a predetermined area in which a first imaging area corresponding to the first imaging and a second imaging area corresponding to the second imaging overlap with each other.

The controller may control the arm so that the X-ray incident angle in the first imaging and the X-ray incident angle in the second imaging are identical to each other in the predetermined area.

The X-ray apparatus may further include an image processor, wherein the image processor generates a combination image by combining a first image obtained by a first imaging and a second image obtained by a second imaging.

The image processor may generate the combination image by adjusting a magnification or reduction ratio of the first image and a magnification or reduction ratio of the second image based on a distance between the object and the detector.

The detector may maintain a constant angle with respect to the object regardless of the movement of the detector.

The X-ray apparatus may further include: an arm connection unit for connecting the supporting unit to the arm; a source connection unit for connecting the source to the arm; and a detector connection unit for connecting the detector to the arm, wherein the source connection unit and the detector connection unit are positioned below the arm connection unit.

The controller may control the arm to locate the detector at a position that is the same as or above a detector base position which is a position of the detector when an X-ray irradiation angle of the source is perpendicular to an X-ray detection side of the detector.

According to an aspect of an exemplary embodiment, there is provided a method of capturing an X-ray image by using an X-ray apparatus that includes a source, a detector, an arm for connecting the source to the detector, and a supporting unit for supporting the arm, the method including: emitting X-rays to an object; detecting the X-rays penetrating the object; and capturing an X-ray image by driving the arm to move the detector up and down according to a rotation of the source.

The capturing of the X-ray image may include: performing a first imaging of detecting the X-rays penetrating the object by using the detector; controlling at least one of the source, the detector, and the arm, in order to perform a second imaging, based on an incident angle of the X-rays that are emitted from the source to the detector in the first imaging; and performing a second imaging of detecting X-rays penetrating the object by using the detector.

The controlling of the at least one of the source, the detector, and the arm may include controlling a straight movement distance of an end of the arm connected to the detector.

The controlling of the straight movement distance may include controlling the arm so that the X-ray incident angle in the first imaging and an X-ray incident angle in the second imaging correspond to each other, in a predetermined area in which a first imaging area corresponding to the first imaging and a second imaging area corresponding to the second imaging overlap with each other.

The controlling of the straight movement distance may include controlling the arm so that the X-ray incident angle in the first imaging and the X-ray incident angle in the second imaging are identical to each other in the predetermined area.

The method may further include generating a combination image by combining a first image obtained by the first imaging and a second image obtained by the second imaging.

The generating of the combination image may include generating the combination image by adjusting a magnification or reduction ratio of the first image and a magnification or reduction ratio of the second image based on a distance between the object and the detector.

The detector may maintain a constant angle with respect to the object in the capturing of the X-ray image.

The X-ray apparatus may further include: an arm connection unit for connecting the supporting unit to the arm; a source connection unit for connecting the source to the arm; and a detector connection unit for connecting the detector to the arm, wherein the source connection unit and the detector connection unit are positioned below the arm connection unit.

The capturing of the X-ray image may include controlling the arm to locate the detector at a position that is the same as or above a detector base position which is a position of the detector when an X-ray irradiation angle of the source is perpendicular to an X-ray detection side of the detector.

According to an aspect of an exemplary embodiment, there is provided a method of obtaining an X-ray image, the method including: performing a first imaging of emitting X-rays from a source connected to one end of an arm to an object and of detecting the X-rays penetrating the object by using a detector connected to the other end of the arm; moving the detector up and down according to the rotation of the source based on an incident angle of the X-rays that are emitted from the source to the detector; performing a second imaging of emitting X-rays from the source to the object and of detecting the X-rays penetrating the object by using the detector; and obtaining the X-ray image, wherein the obtaining of the X-ray image includes: adjusting a magnification or reduction ratio of a first image obtained in the first imaging and a magnification or reduction ratio of a second image obtained in the second imaging based on a distance between the object and the detector, and generating a combination image by combining the first image and the second image each of which magnification or reduction ratio has been adjusted.

According to an X-ray apparatus according to an exemplary embodiment, a method of capturing an X-ray image by using the X-ray apparatus, and a method of obtaining an X-ray image by using the X-ray apparatus, a plurality of images may be stitched without distortion. Accordingly, a highly accurate image for a large area may be obtained.

BRIEF DESCRIPTION OF THE DRAWINGS

The above and/or other aspects will become more apparent by describing certain exemplary embodiments, with reference to the accompanying attached drawings, in which:

FIGS. 2A, 2B, and 2C are diagrams illustrating a stepping method-based imaging operation of an X-ray apparatus;

FIGS. 4A, 4B, 4C, and 4D are diagrams illustrating actual images captured according to a stepping method-based imaging;

FIG. 11 is a flowchart illustrating a method of obtaining an X-ray image, according to an exemplary embodiment.

DETAILED DESCRIPTION

Figure 1:
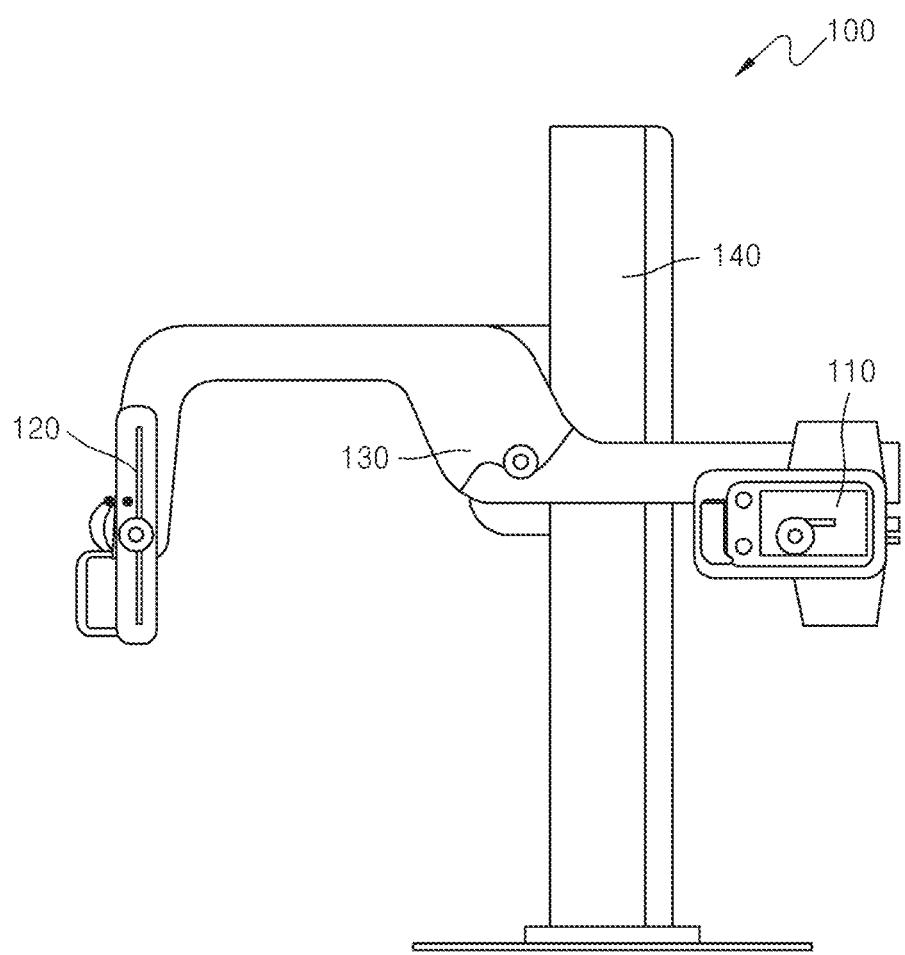
FIG. 1 is a diagram illustrating the structure of an X-ray apparatus.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

The terms used in the present specification are used for explaining a certain exemplary embodiments, and are not limiting the present inventive concept. Thus, the expression of singularity in the present specification includes the expression of plurality unless clearly specified otherwise in context. Unless defined otherwise, all terms used herein including technical or scientific terms have the same meanings as those generally understood by those skilled in the art to which the present inventive concept may pertain. The terms as those defined in generally used dictionaries are construed to have meanings matching that in the context of related technology and, unless clearly defined otherwise, are not construed to be ideally or excessively formal.

When a part may "include" a certain element, unless specified otherwise, it is not to be construed to exclude another element but may be construed to further include other elements. The terms such as "~portion", "~unit", "~module", and "~block" stated in the specification may signify a unit to process at least one function or operation and the unit may be embodied by hardware, software, or a combination of hardware and software. Expressions such as "at least one of," when preceding a list of elements, modify the entire list of elements and do not modify the individual elements of the list.

FIG. 1 is a diagram illustrating the structure of an X-ray apparatus 100. Referring to FIG. 1, the X-ray apparatus 100 includes a source 110 for emitting X-rays to an object and a detector 120 for detecting the X-rays penetrating the object. For example, the X-ray apparatus 100 further includes an arm 130 for connecting the source 110 to the detector 120 and a supporting unit 140 for supporting the arm 130.

FIGS. 2A through 2C are diagrams illustrating a stepping method imaging operation of the X-ray apparatus 100. The X-ray apparatus 100 illustrated in FIG. 1 may image the object by using a stepping method. The stepping method is a method of capturing an X-ray image of the object while moving the source 110 and the detector 120.

As illustrated in FIG. 2A, according to the stepping method, X-rays are emitted from the source 210 to the detector 220 perpendicularly to an X-ray detection plane of the detector 220. The object 250 is imaged by detecting the X-rays penetrating the object 250. Hereinafter, imaging illustrated in FIG. 2A is referred to as a first imaging, imaging illustrated in FIG. 2B is referred to as a second imaging, and imaging illustrated in FIG. 2C is referred to as a third imaging.

When the first imaging for the object 250 is completed, the second imaging illustrated in FIG. 2B and the third imaging illustrated in FIG. 2C are sequentially performed while moving the detector 220 and the source 210, in a direction 230. During the first, second, and third imaging, an angle of irradiation of the X-rays from the source 210 to the detector 220 and a distance from the source 210 to the detector 220 are maintained constant and only the heights of the source 210 and detector 220 from the ground are changed. According to the stepping method, a large area of an object may be imaged through a plurality of imaging operations. However, image distortion may occur when combining a plurality of images, captured by the stepping method, to make a single image, that is, when performing an image stitching technique.

Figure 3A:
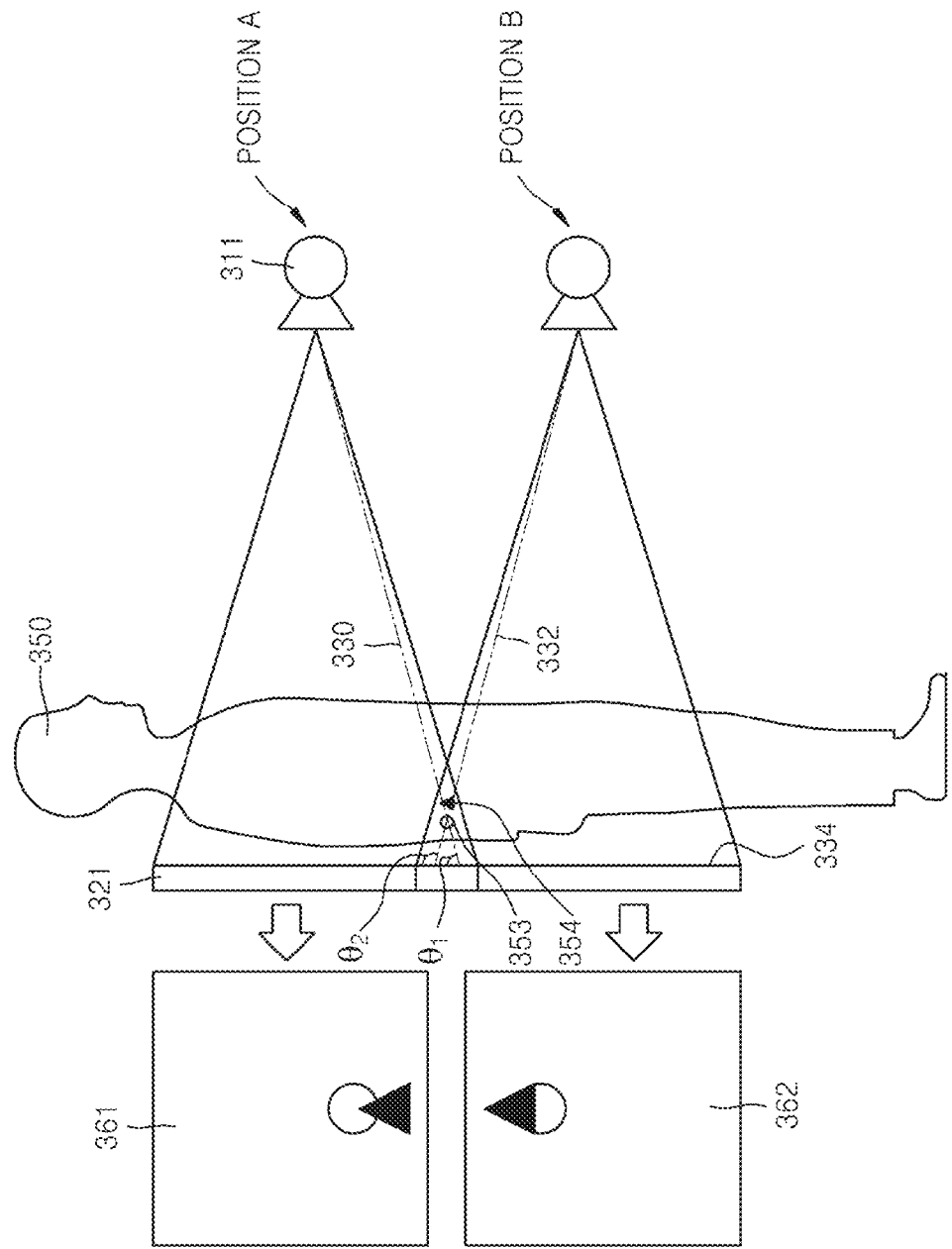
FIGS. 3A and 3B are diagrams for explaining image distortion occurring due to a stepping method-based imaging.
Figure 3B:
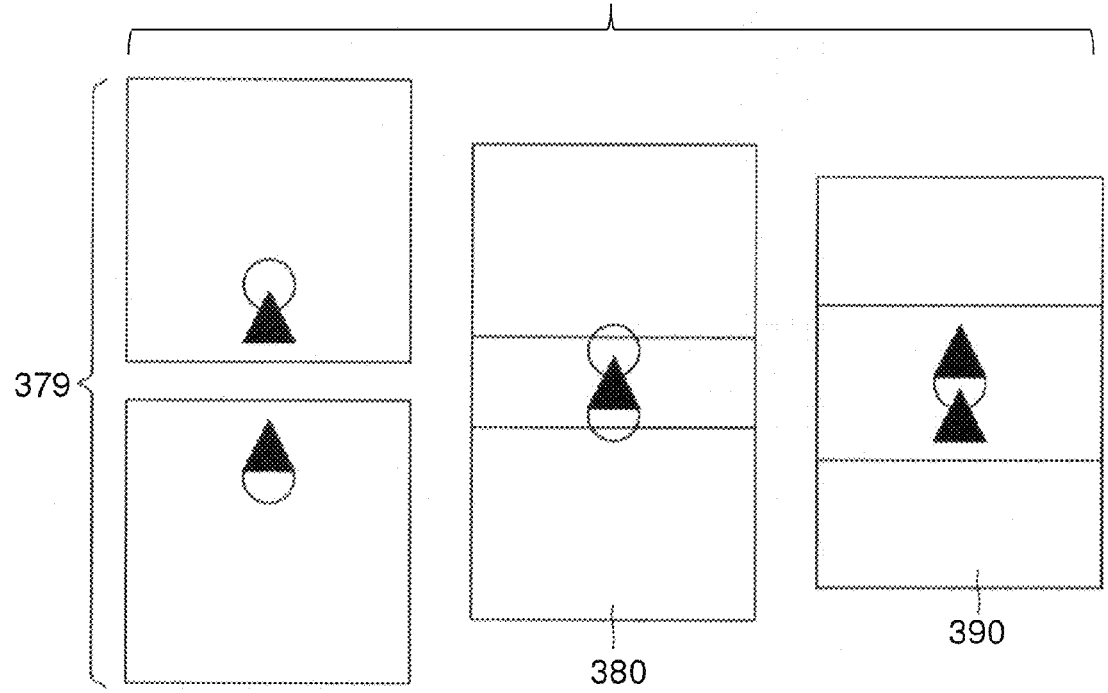

Below, image distortion occurring due to an imaging using the stepping method is described with reference to FIGS. 3A and 3B. FIG. 3A illustrates a first image 361 obtained as a detector 321 detects X-rays penetrating an object 350 after being emitted from a source 311 at a position A. A second image 362 is obtained as a detector 321 detects X-rays penetrating the object 350 after being emitted from a source 311 at a position B.

Referring to FIG. 3A, in the object 350, a first tissue 353 indicated as a circle and a second tissue 354 indicated as a triangle are positioned at the same height. However, relative positions of the first tissue 353 and the second tissue 354, which are observed in the first or second images 361 or 362 obtained by detecting the X-rays penetrating the object 350, are different from the actual case. That is, in the first image 361, an image (a circle) of the first tissue 353 is positioned above an image (a triangle) of the second tissue 353. In the second image 362, an image (a circle) of the first tissue 353 is positioned under an image (a triangle) of the second tissue 354.

Such a difference between the positions of the first tissue 353 and second tissue 354 on the first image 361 and the second image 362 is due to a difference between the incident angle of X-rays that are emitted from the source 311 to the detector 321 at the position A and the incident angle of X-rays that are emitted from the source 311 to the detector 321 at the position B.

The incident angle of X-rays that are emitted from a source to a detector is an angle between the X-rays emitted from the source and an X-ray detection plane 334 of the detector. Accordingly, the incident angles of X-rays that are incident on each point of the X-ray detection plane of the detector are different from each other. Referring to FIG. 3A, an incident angle $\Theta_1$ is an angle between the direction of X-rays 330 penetrating the first and second tissues 353 and 354 of the object 350 after the X-rays are emitted from the source 311 at the position A and an X-ray detection plane of the detector 321. An incident angle $\Theta_2$ is an angle between the direction of X-rays 332 penetrating the first and second tissues 353 and 354 of the object 350 after the X-rays are emitted from the source at the position B and an X-ray detection plane of the detector 322. In this case, an incident angle of X-rays penetrating the first and second tissues 353 and 354 is $\Theta_1$ for the first image 361 and $\Theta_2$ for the second image 362, and $\Theta_1$ and $\Theta_2$ are different from each other. Thus, relative positions of the first tissue 353 and the second tissue 354, which are observed in the first image 361, are different from those which are observed in the second image 362.

Accordingly, due to the difference between the positions of the first tissue 353 and second tissue 354 on the first image 361 and the second image 362, image distortion occurs when making a single image by combining the first image 361 and the second image 361, that is, when performing an image stitching.

The image distortion occurring due to the combination of the first image 361 and the second image 362 is described with reference to FIG. 3B. An image 379 shows a state before the first image 361 and the second image 362 are not combined. An image 380 shows an image obtained by combining the first image 361 with the second image 362 based on the image of the second tissue 354. An image 390 shows an image obtained by combining the first image 361 with the second image 362 based on the image of the first tissue 353. Referring to the image 380 and the image 390, image distortion shown as a double image of the first tissue 353 or second tissue 354 occurs in an area in which the first image 361 and the second image 362 overlap with each other.

FIGS. 4A through 4D are diagrams illustrating actual images captured according to the stepping method-based imaging of the X-ray apparatus 100. FIG. 4A illustrates an image captured by imaging a predetermined area of an object. FIG. 4B illustrates an image captured by imaging an area different from the predetermined area of the object. Circles 401 and 402 indicate an area of the object, which is repeatedly imaged. Referring to the circle 401 of FIG. 4A and the circle 402 of FIG. 4B, an image of the circle 401 and an image of the circle 402 are not matched with each other although the same area of the object has been imaged.

Referring to FIGS. 4C and 4D which schematically illustrate FIGS. 4A and 4B, such an image mismatching is easily understood. A position relation between a first tissue indicated by dots and a second tissue indicated by slashes, illustrated in FIG. 4C, is different from that illustrated in FIG. 4D. Accordingly, image distortion occurs when stitching two images, that is, the image illustrated in FIG. 4C and the image illustrated in FIG. 4D. Thus, an exemplary embodiment provides an X-ray apparatus that may minimize image distortion occurring when performing a stitching to obtain an image for a large area. Also, the present invention provides a method of capturing an X-ray image by using the X-ray apparatus.

Figure 5:
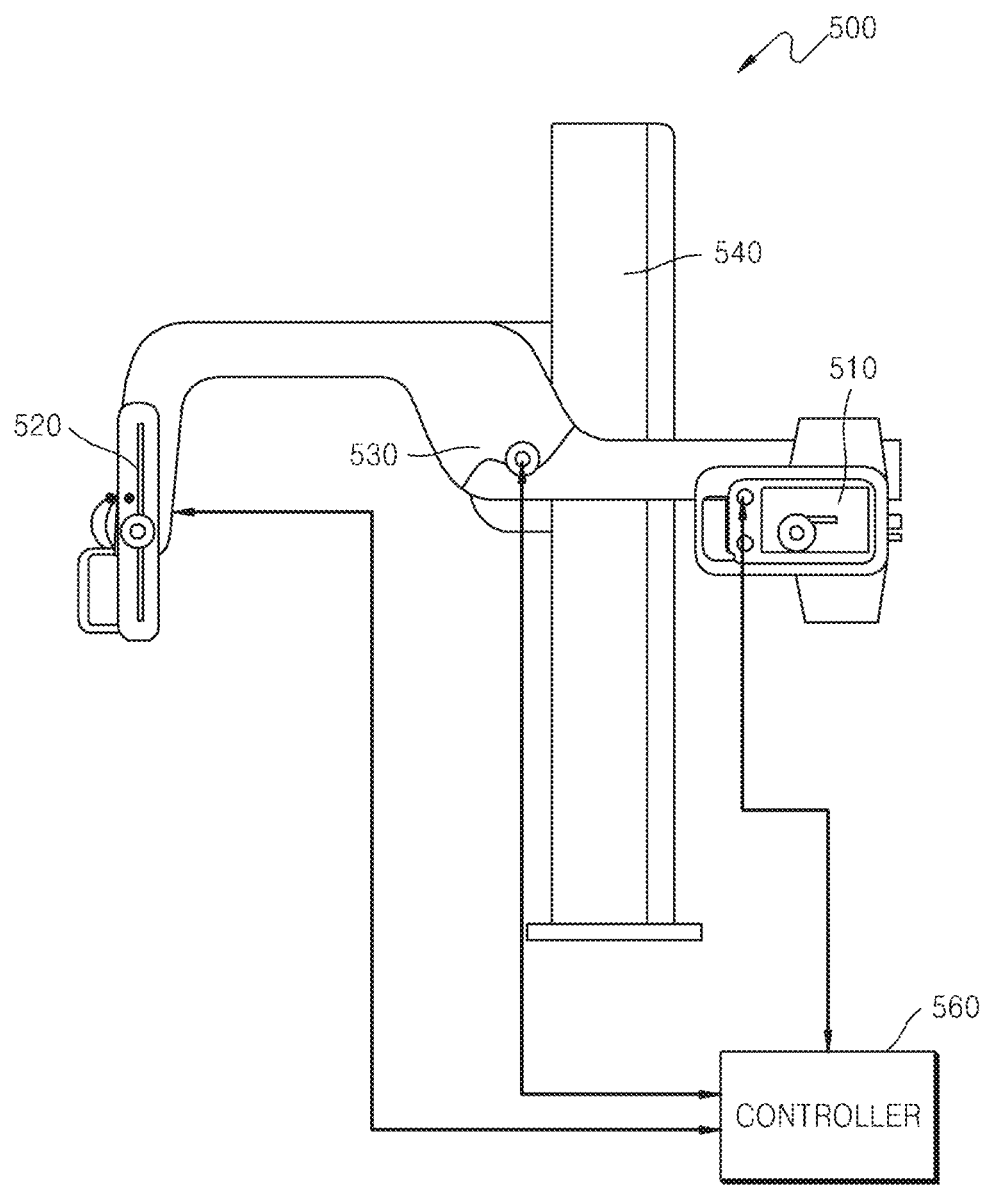
FIG. 5 is a diagram illustrating an X-ray apparatus according to an exemplary embodiment.

FIG. 5 is a diagram illustrating an X-ray apparatus 500 according to an exemplary embodiment.

Referring to FIG. 5, the X-ray apparatus 500 includes a source 510, a detector 520, an arm 530, a supporting unit 540, and a controller 560. The source 510 emits X-rays to an object, and the detector 520 detects the X-rays penetrating the object. The arm 530 connects the source 510 to the detector 520, and moves the detector 520 up and down according to the rotation or movement of the source 510. The detector 520 may maintain a constant angle with respect to the object regardless of up and down movement. The support unit 540 supports the arm 530, and the controller 560 controls the imaging of the object by driving the arm 530. An operation of the X-ray apparatus 500 is described with reference to FIG. 6 below.

The controller 560 controls at least one of the source 510, the detector 520, and the arm 530, and may control the arm 530 connected to the detector 520, in order to perform a second imaging, based on an incident angle of X-rays that are emitted from the source 510 to the detector 520 during a first imaging. In this case, the arm 530 may be controlled to be rotated on the support unit 540 or to be moved up and down, and the controller 560 may move the detector 520 by controlling a straight movement distance of an end of the arm 530 connected to the detector 520. In detail, the controller 560 may control the straight movement distance of the end of the arm 530 connected to the detector 520, and may vertically move the detector 520 according to the straight movement distance.

Controlling the arm 520 based on an X-ray incident angle may be controlling the arm 520 so that an X-ray incident angle in a first imaging and an X-ray incident angle in a second imaging correspond to each other, in a predetermined area in which a first imaging area corresponding to the first imaging and a second imaging area corresponding to the second imaging overlap with each other. For example, the controlling of the arm 520 based on an X-ray incident angle may be controlling the arm 520 so that in the predetermined area, a difference between the X-ray incident angle in the first imaging and the X-ray incident angle in the second imaging is within a predetermined acceptable range. The predetermined acceptable range means a difference between the X-ray incident angle in the first imaging and the X-ray incident angle in the second imaging, which allows at least two tissue areas positioned at the same point (for example, the first and second tissues 353 and 354 illustrated in FIG. 3A) to be shown to be positioned at the same point in the first imaging area (for example, the first image 361 of FIG. 3A) and the second imaging area (for example, the second image 362 of FIG. 3A). For example, the controlling of the arm 520 based on an X-ray incident angle may be controlling the arm 520 so that the X-ray incident angle in the first imaging and the X-ray incident angle in the second imaging are identical to each other in the predetermined area.

Figure 6:
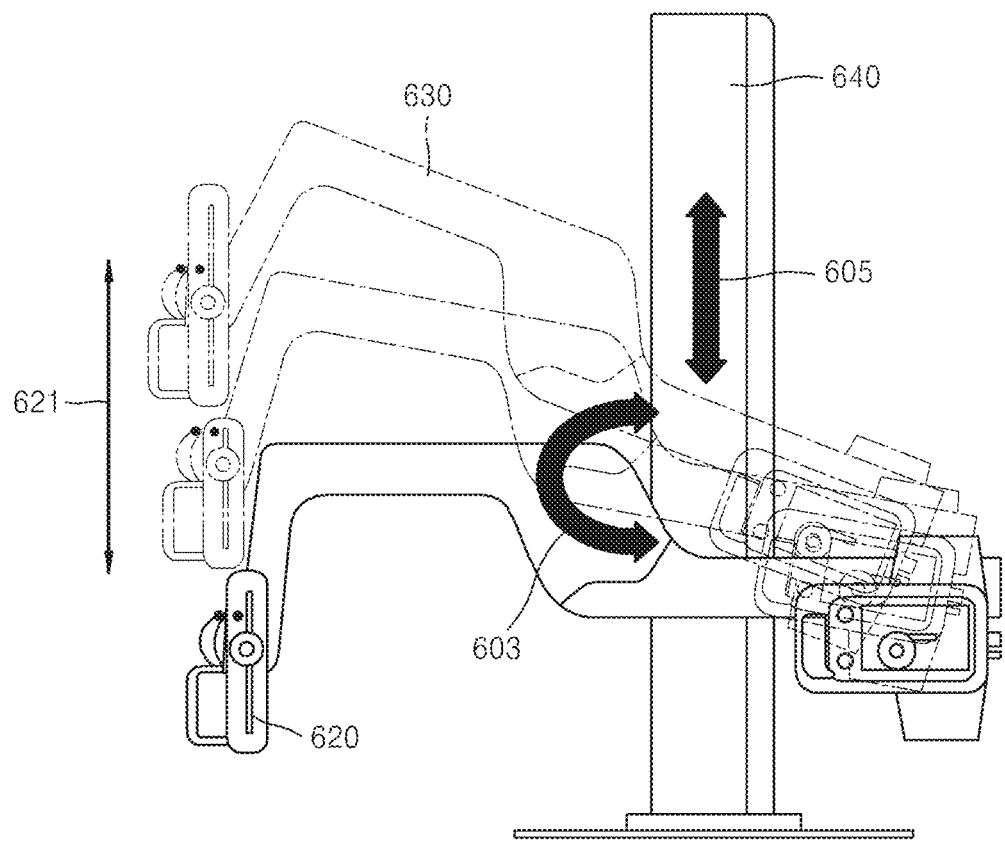
FIG. 6 is a diagram illustrating an operation of an X-ray apparatus according to an exemplary embodiment.

FIG. 6 is a diagram illustrating an operation of the X-ray apparatus according to an exemplary embodiment. An arm 630 and supporting unit 640 illustrated in FIG. 6 correspond to the arm 530 and supporting unit 540 illustrated in FIG. 5, and thus, descriptions overlapping with those of FIG. 5 are not repeated.

As illustrated in FIG. 6, the arm 630 may rotate as indicated by an arrow 603 with respect to the supporting unit 640, and may also move up and down as indicated by an arrow 605. For example, the detector 620 positioned in the end of the arm 630 may move straight as indicated by an arrow 621 to correspond to the rotation or to the up and down movement of the arm 630.

Figure 7A:
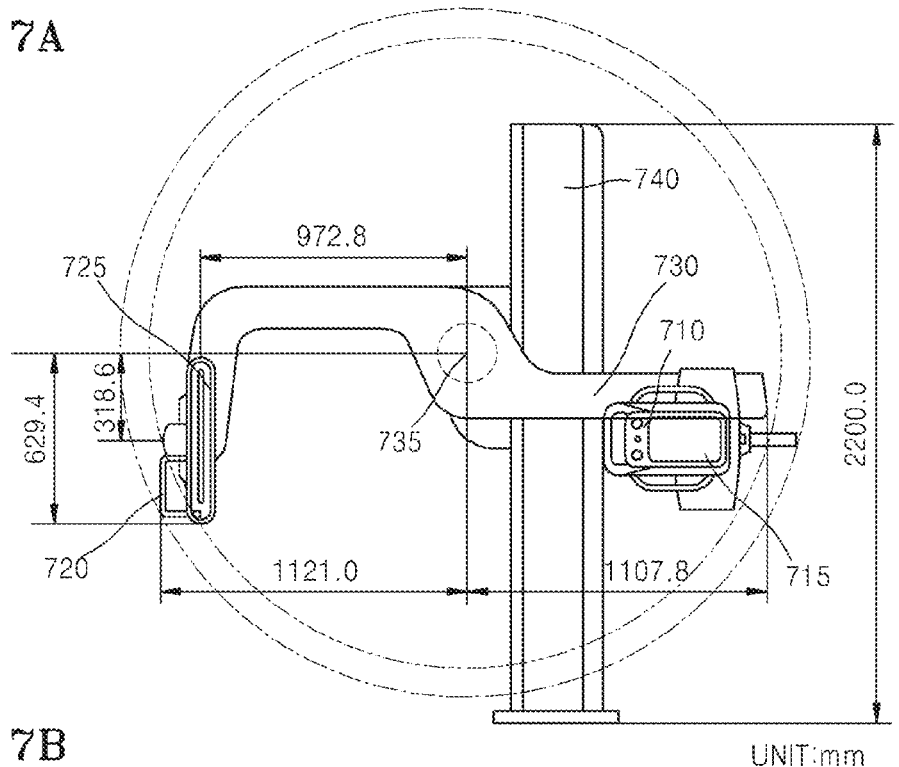
FIGS. 7A and 7B are diagrams for explaining a simulation imaging using an X-ray apparatus according to an exemplary embodiment.
Figure 7B:
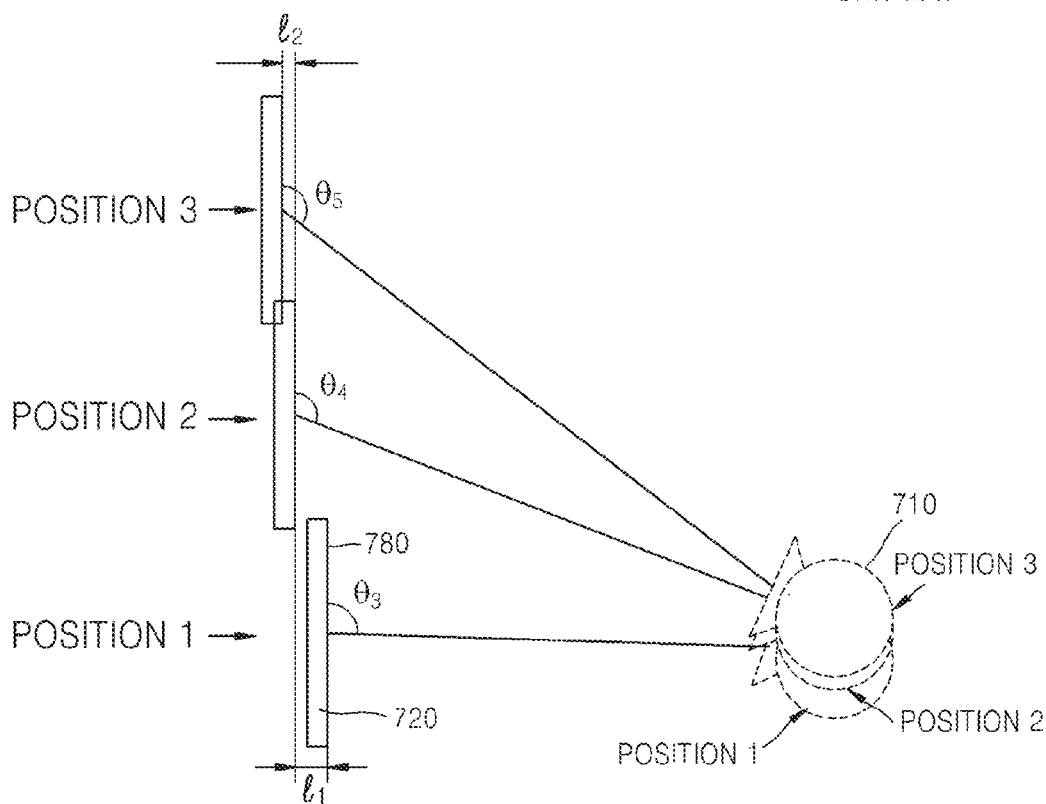

FIGS. 7A and 7B are diagrams for explaining a simulation imaging using the X-ray apparatus according to an exemplary embodiment. The X-ray apparatus illustrated in FIG. 7A is used for simulation. The X-ray apparatus of FIG. 7A includes a source 710, a detector 720, an arm 730, a supporting unit 740, and a controller (not shown). For example, the X-ray apparatus of FIG. 7A may further include an arm connection unit 735 for connecting the supporting unit 740 to the arm 730, a source connection unit 715 for connecting the source 710 to the arm 730, and a detector connection unit 725 for connecting the detector 720 to the arm 730. The source connection unit 715 may be the center on which the source 710 rotates, the detector connection unit 725 may be the center on which the detector rotates, and the arm connection unit 735 may be the center on which the arm 730 rotates.

In order to stably drive the arm 730, the detector 720 and the source 710 are positioned below the arm 730 in consideration of the weight of the detector 720 and source 710. That is, the source connection unit 715 and the detector connection unit 725 may be positioned below the arm connection unit 735. For example, an imaging of an object may be performed by controlling the arm 730 to locate the detector 720 above a base position or a first position. The base position of the detector 720 is a position of the detector 720 when an X-ray irradiation angle of the source 710 is perpendicular to an X-ray detection plane of the detector 720. The X-ray irradiation angle of the source 710 is an angle between the center point of the X-ray detection plane of the detector 720 and the source 710.

FIG. 7A illustrates the X-ray apparatus in which the detector 720 is positioned at the base position. As illustrated in FIG. 7A, the source connection unit 715 and the detector connection unit 725 are positioned below the arm connection unit 735, and an object may be imaged by controlling the arm 730 to locate the detector 720 above the base position, to alleviate a possibility of a collision which may occur as a distance between the detector 720 and the object may rapidly shorten when the detector 720 moves below the base position while the arm 730 rotates. For example, as illustrated in FIG. 7B, the position 1 is the base position and the arm 730 may be controlled to locate the detector 720 at a position 1 or above the position 1 (for example, at a position 2 or at a position 3).

Figure 8:
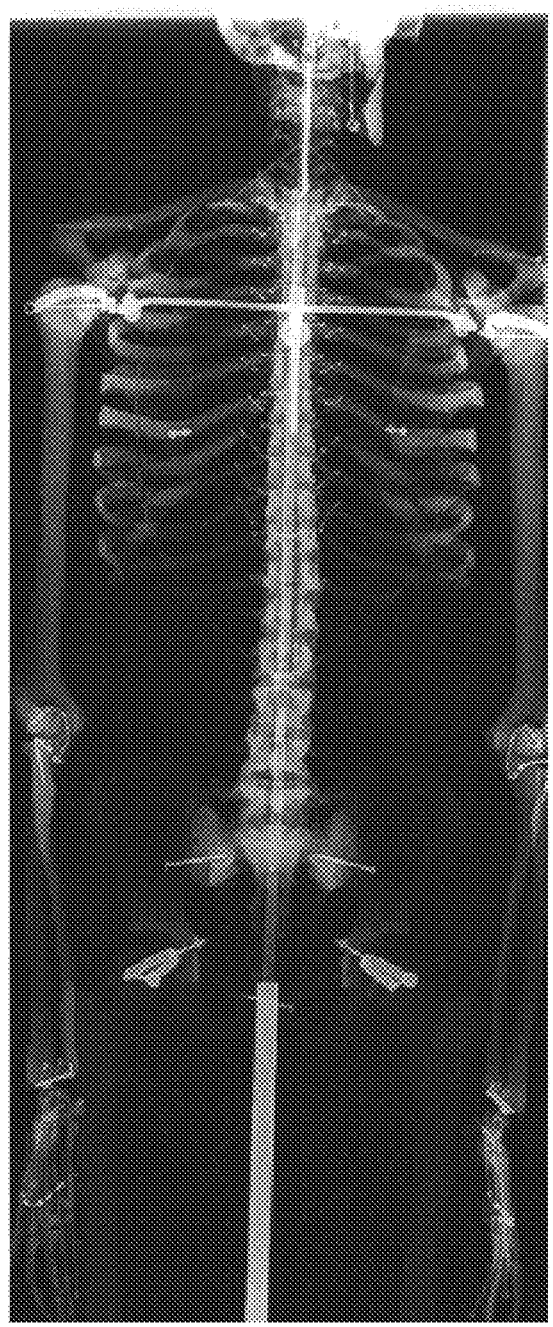
FIG. 8 illustrates a simulation result image obtained using an X-ray apparatus according to an exemplary embodiment.

FIG. 7B is a diagram schematically illustrating an operation of the X-ray apparatus of FIG. 7A, used for simulation. The X-ray apparatus controls the arm 730 to move the detector 720 from the position 1 to the position 2 and from the position 2 to the position 3 while overlapping the positions with each other by approximately 5 cm. FIG. 8 illustrates a result obtained through the stitching of an image captured by moving the detector 720 upward while increasing an angle of the arm 730 by 12°. The angle of the arm 730 is an angle between the arm 730 and the X-ray detection plane 780 of the detector 720. In the current simulation, the angle of the arm 730 is controlled so as to coincide with the X-ray irradiation angle of the source 710. $\Theta_3$ indicates the angle of the arm 730 in an imaging performed in the position 1, $\Theta_4$ indicates the angle of the arm 730 in an imaging performed in the position 2, and $\Theta_5$ indicates the angle of the arm 730 in an imaging performed in the position 3. In FIG. 7B, the arm 730 is not illustrated. The detector 720 is moved perpendicularly to the ground, i.e., in a direction substantially perpendicular to a horizontal line of the earth. In the current simulation, detailed driving coordinates of the X-ray apparatus are indicated in Table 1.

TABLE 1

| Position | Angle of Arm (°) | Height of Arm (mm) | Detector Push (mm) |
|---|---|---|---|
| 1 | 90 | 0 | 0 |
| 2 | 102 | 165 | 44 |
| 3 | 114 | 320 | 4 |

As illustrated in Table 1, an imaging was performed while increasing the angle of the arm 730 by 12° and increasing the height of the arm 730, based on the position 1. When the arm 730 is controlled as illustrated in Table 1, a difference between an X-ray incident angle in a previous imaging and an X-ray incident angle in a next imaging is placed within the range of ±0.3° in a predetermined area in which imaging areas of the detector 720 overlap with each other.

The detector 720 moves away from the object as the angle and height of the arm 730 are controlled, and the extent that the detector 720 is pushed is shown in Table 1. Referring to FIG. 7B, the detector push generated when the detector 720 moves from the position 1 to the position 2 is illustrated as $l_1$, and the detector push generated when the detector 720 moves from the position 2 to the position 3 is illustrated as $l_2$. The image of the object that is detected by the detector 720 is magnified when the object becomes more distant from the detector 720, and is reduced when the object gets closer to the detector 720. Accordingly, the X-ray apparatus may further include an image processor (not shown) that adjusts a magnification or reduction ratio of the image of the object based on a distance between the object and the detector 720 and generates a combination image based on the adjusted magnification or reduction ratio. The image processor is described with reference to FIG. 9 below.

FIG. 8 is a diagram illustrating a simulation result image obtained using the X-ray apparatus illustrated in FIG. 7A. As can be observed from the simulation result image of FIG. 8, the images captured according to an exemplary embodiment exhibit an undistorted stitching of separate overlapping images. A seamless image for a large area of the object is shown in FIG. 8.

Figure 9:
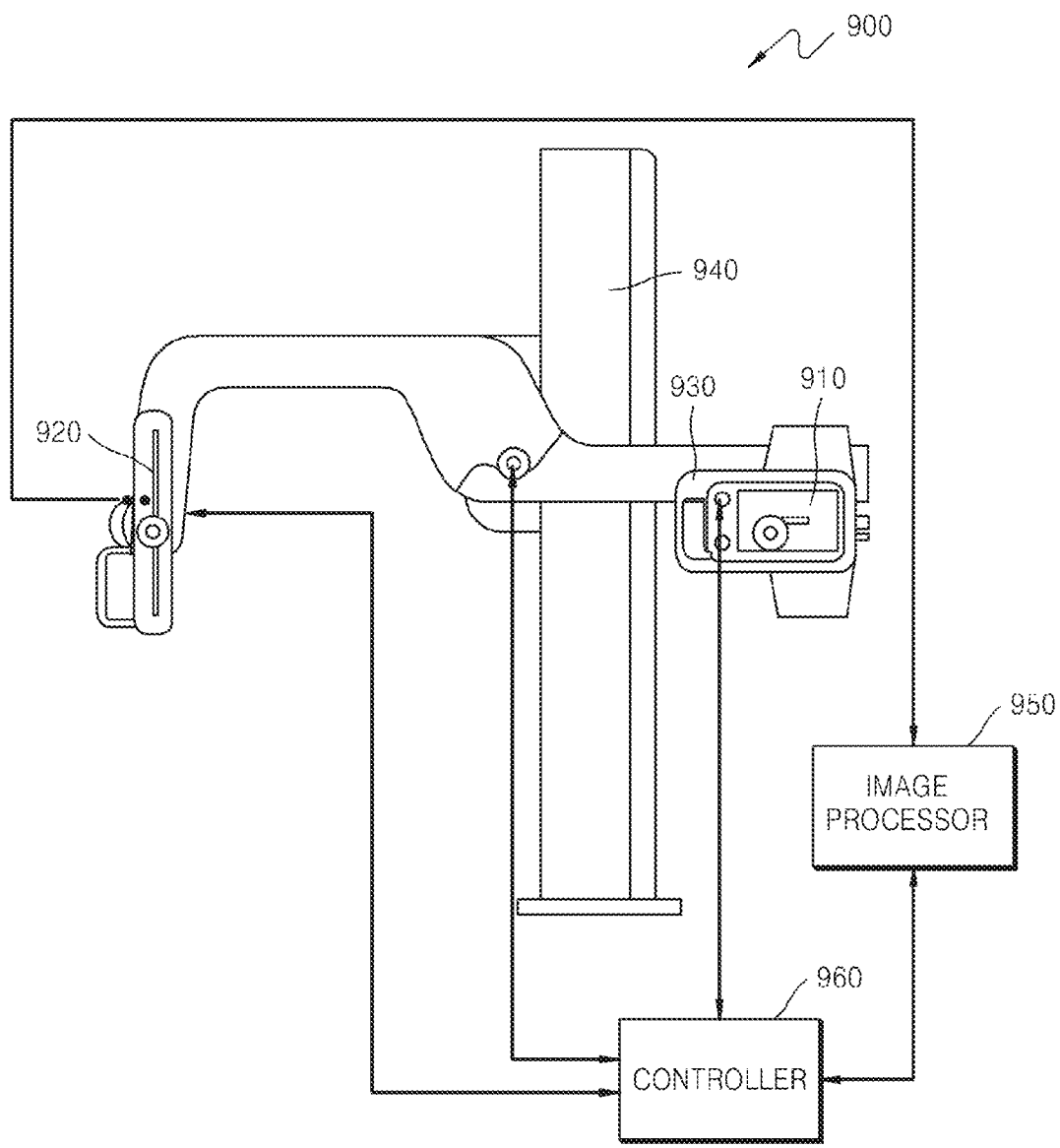
FIG. 9 is a diagram illustrating an X-ray apparatus according to an exemplary embodiment.

FIG. 9 is a diagram illustrating an X-ray apparatus 900 according to an exemplary embodiment.

Referring to FIG. 9, the X-ray apparatus 900 includes a source 910, a detector 920, an arm 930, a supporting unit 940, a controller 960, and an image processor 950. The source 910, the detector 920, the arm 930, the supporting unit 940, and the controller 960, illustrated in FIG. 9, correspond to the source 510, the detector 520, the arm 530, the supporting unit 540, and the controller 560, illustrated in FIG. 5, respectively. Thus, descriptions overlapping with those of FIG. 5 are not repeated.

The image processor 950 may generate a combination image by combining images obtained by the detector 920 that detects X-rays penetrating an object. For example, the image processor 950 may adjust a magnification or reduction ratio of the image of the object based on a distance between the object and the detector 920 and may generate the combination image based on the adjusted magnification or reduction ratio.

Figure 10:
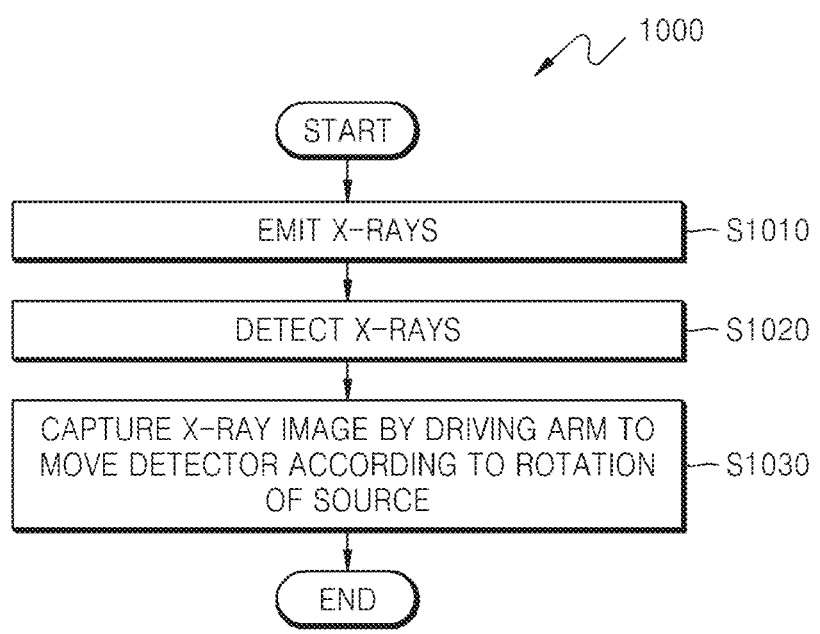
FIG. 10 is a flowchart illustrating a method of capturing an X-ray image, according to an exemplary embodiment.

FIG. 10 is a flowchart illustrating a method 1000 of capturing an X-ray image, according to an exemplary embodiment.

The method 1000 of capturing an X-ray image may be performed by the X-ray apparatus 500 described with reference to FIG. 5. Operations of the method 1000 of capturing an X-ray image are substantially the same as the operations of the X-ray apparatus 500. Accordingly, descriptions overlapping with those of FIG. 5 are not repeated.

Referring to FIG. 10, the X-ray apparatus 500 performs an operation of emitting X-rays to an object (operation S1010), an operation of detecting the X-rays penetrating the object (operation S1020), and an operation of capturing an X-ray image by driving the arm 530 to move the detector 520 up and down according to a rotation of the source 510 (operation S1030). The operation S1010 of emitting the X-rays may be performed by the source 510, the operation S1020 of detecting the X-rays may be performed by the detector 520, and the operation S1030 of capturing the X-ray image may be performed by the controller 560.

FIG. 11 is a flowchart illustrating a method 1100 of obtaining an X-ray image, according to an exemplary embodiment.

The method 1100 of obtaining an X-ray image may be performed by the X-ray apparatus 900 described with reference to FIG. 9. Operations of the method 1100 of obtaining an X-ray image are substantially the same as the operations of the X-ray apparatus 900. Accordingly, descriptions overlapping with those of FIG. 9 are not repeated.

Referring to FIG. 11, the X-ray apparatus 900 performs a first imaging operation of emitting X-rays from the source 910 to an object and of detecting the X-rays penetrating the object by using the detector 920 (operation S1110), an operation of moving the detector 920 up and down according to the rotation of the source 910 based on an incident angle of X-rays that are emitted from the source 910 to the detector 920 (operation S1120), and a second imaging operation of emitting X-rays from the source 910 to the object and of detecting the X-rays penetrating the object by using the detector 920 (operation S1130). For example, the X-ray apparatus 900 performs an operation of adjusting a magnification or reduction ratio of a first image obtained in the first imaging operation and a magnification or reduction ratio of a second image obtained in the second imaging operation based on a distance between the object and the detector 920 (operation S1140), and an image obtaining operation of generating a combination image by combining the first image and the second image each of which magnification or reduction ratio has been adjusted (operation S1150).

Although a few exemplary embodiments have been shown and described, exemplary embodiments are not limited thereto. It would be appreciated by those skilled in the art that changes may be made in these exemplary embodiments without departing from the principles and spirit of the disclosure, the scope of which is defined in the claims and their equivalents.

What is claimed is:

1. An X-ray apparatus comprising:
a source configured to emit X-rays to an object;
a detector configured to detect the X-rays that have been penetrated the object;
an arm configured to connect the source to the detector and move the detector up and down according to a rotation of the source;
and
a controller configured to control an imaging of the object by driving the arm.

2. The X-ray apparatus of claim 1, wherein the controller is further configured to control a straight movement distance of an end of the arm connected to the detector based on an X-ray incident angle of X-rays that are emitted from the source to the detector.

3. The X-ray apparatus of claim 1, wherein the controller is further configured to control a straight movement distance of an end of the arm connected to the detector, to image a second imaging area of the object in a second imaging operation, based on a first X-ray incident angle of the X-rays in a first imaging area of the object imaged in a first imaging operation.

4. The X-ray apparatus of claim 3, wherein the controller is further configured to control the arm so that the first X-ray incident angle and a second X-ray incident angle of the X-rays in the second imaging area imaged in the second imaging operation substantially correspond to each other, in at least a portion of an area in which the first imaging area and the second imaging area overlap with each other.

5. The X-ray apparatus of claim 4, wherein the controller is further configured to control the arm so that the first X-ray incident angle and the second X-ray incident angle are identical to each other.

6. The X-ray apparatus of claim 1, further comprising an image processor configured to generate a combination image by combining a first image and a second image obtained by imaging a first area and a second area of the object, respectively, in a first imaging operation and a second imaging operation.

7. The X-ray apparatus of claim 6, wherein the image processor is configured to generate the combination image by adjusting a magnification or reduction ratio of the first image and a magnification or reduction ratio of the second image based on a distance between the object and the detector.

8. The X-ray apparatus of claim 1, wherein the detector is configured to maintain a constant angle with respect to the object regardless of the movement of the detector.

9. The X-ray apparatus of claim 1, further comprising:
   a support unit which supports the arm;
   an arm connection unit which connects the supporting unit to the arm;
   a source connection unit which connects the source to the arm; and
   a detector connection unit which connects the detector to the arm,
   wherein the source connection unit and the detector connection unit are positioned below the arm connection unit.

10. The X-ray apparatus of claim 9, wherein the controller is configured to control the arm to locate the detector at a position that is the same as or above a first position which is a position of the detector when an X-ray irradiation angle of the source is perpendicular to an X-ray detection plane of the detector.

11. A method of capturing an X-ray image, the method comprising:
   emitting X-rays to an object, by a source;
   detecting the X-rays that have penetrated the object, by a detector; and
   capturing an X-ray image by driving an arm connected between the source and the detector, to move the detector up and down according to a rotation of the source.

12. The method of claim 11, wherein the capturing the X-ray image comprises:
   performing a first imaging by detecting the X-rays which have penetrated a first imaging area of the object;
   controlling at least one of the source, the detector, and the arm, to perform a second imaging, based on a first incident angle of the X-rays that are emitted from the source in the first imaging; and
   performing a second imaging by detecting X-rays which have penetrated a second imaging area of the object.

13. The method of claim 12, wherein the controlling comprises controlling a straight movement distance of an end of the arm connected to the detector.

14. The method of claim 13, wherein the controlling the straight movement distance comprises:
   controlling the arm so that the first incident angle and a second incident angle of the X-rays in the second imaging substantially correspond to each other, in at least a portion of an area in which the first imaging area and the second imaging area overlap with each other.

15. The method of claim 14, wherein the controlling the straight movement distance comprises controlling the arm so that the first incident angle and the second incident angle are identical to each other.

16. The method of claim 12, further comprising generating a combination image by combining a first image obtained by the first imaging and a second image obtained by the second imaging.

17. The method of claim 16, wherein the generating the combination image comprises generating the combination image by adjusting a magnification or reduction ratio of the first image and a magnification or reduction ratio of the second image based on a distance between the object and the detector.

18. The method of claim 11, wherein the capturing comprises:
   maintaining a constant angle of the detector with respect to the object.

19. The method of claim 11, wherein the arm is supported by a supporting unit which is connected to the arm by an arm connection unit, the source is connected to the arm by a source connection unit, and the detector is connected to the arm by a detector connection unit, and
   the method further comprises positioning the source connection unit and the detector connection unit below the arm connection unit.

20. The method of claim 19, wherein the capturing the X-ray image comprises:
   controlling the arm to locate the detector at a position that is the same as or above a first position which is a position of the detector when an X-ray irradiation angle of the source is perpendicular to an X-ray detection plane of the detector.

21. A method of obtaining an X-ray image, the method comprising:
   performing a first imaging by emitting X-rays from a source connected to a first end of an arm to an object and detecting the X-rays that have penetrated the object by a detector connected to a second end of the arm;
   moving the detector up and down according to a rotation of the source based on an incident angle of the X-rays that are emitted from the source;
   performing a second imaging by emitting X-rays from the source to the object and detecting the X-rays that have penetrated the object, by the detector; and
   obtaining the X-ray image by adjusting a magnification or reduction ratio of a first image obtained in the first imaging and a magnification or reduction ratio of a second image obtained in the second imaging based on a distance between the object and the detector, and generating a combination image by combining the first image and the second image in each of which the magnification or reduction ratio has been adjusted.

\* \* \* \* \*